United States Patent [19]
Matsumura

[11] 3,936,844
[45] Feb. 3, 1976

[54] EYE-FUNDUS CAMERA EASY FOR ALIGNMENT OF PUPIL

[75] Inventor: Isao Matsumura, Yokohama, Japan

[73] Assignee: Canon Kabushiki Kaisha, Japan

[22] Filed: Mar. 18, 1974

[21] Appl. No.: 452,252

[30] Foreign Application Priority Data
Mar. 22, 1973  Japan.............................. 48-33745

[52] U.S. Cl. ................................................ 354/62
[51] Int. Cl.² ........................................ G03B 29/00
[58] Field of Search ...................................... 354/62

[56] References Cited
UNITED STATES PATENTS
3,217,622  11/1965  Kiyono................................ 354/62

Primary Examiner—John M. Horan
Attorney, Agent, or Firm—Toren, McGeady and Stanger

[57] ABSTRACT

The present invention relates to an improvement of the alignment system for the pupil in an eye-fundus camera. An auxiliary lens is provided so as to be freely inserted and pulled out at an optical path behind an object lens in an optical system for observing and photographing an eye fundus wherein said auxiliary lens is inserted at the same position as that of an image of the eye fundus which is formed by said object lens when said auxiliary lens is not inserted. Thus the image of a pupil is formed so that observation of the pupil becomes possible by an eye-fundus observation finder and the alignment of the pupil becomes easy.

7 Claims, 2 Drawing Figures

EYE-FUNDUS CAMERA EASY FOR ALIGNMENT OF PUPIL

BACKGROUND OF THE INVENTION

1. Field of the Invention

The present invention relates to an alignment system for the pupil in an eye-fundus camera.

2. Disclosure of prior Art

In an eye-fundus camera, a so-called alignment system for the pupil is necessary so as to have the optical axis of an object lens match with the center of the pupil of an eye to be examined when it is used. For that end in one prior art approach, the pupil alignment is done by observing from the outside of a camera the manner in which the illuminating light which is incident upon an eye to be examined passes through the object lens. And for that it is necessary for the observer to come out of an observation finder for the eye-fundus image so as to peep in by stretching oneself to front right (or front left) direction. Thus observation work is inconvenient, and when the distance between the eye being examined and the object lens is short, there is such inconvenience since it is difficult to peep in.

BRIEF SUMMARY OF THE INVENTION

Thus the object of the present invention is to provide an eye-fundus camera in which the above mentioned shortcomings are eliminated by that a pupil of the eye being examined can be observed with a finder for observing an eye-fundus image by providing an auxiliary lens which may be freely pulled out and inserted behind an object lens.

Figure 1:
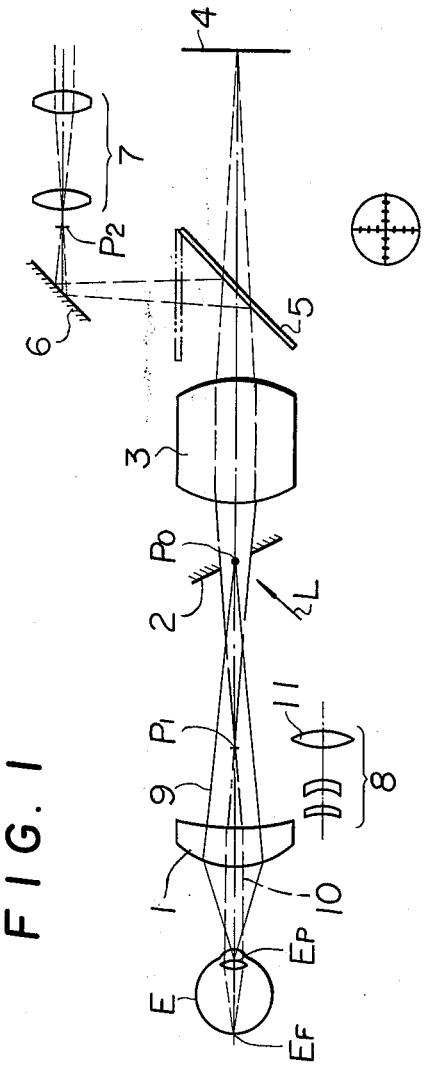
FIG. 1 is a drawing to explain an eye-fundus camera of the present invention in a state wherein an auxiliary lens is not inserted, and an imaging relationship between the eye-fundus image and the pupil image at such state.

DETAILED DESCRIPTION OF INVENTION:

An example of the present invention will be explained in detail referring to the drawings. In the drawings 1 is an object lens, 2 is a mirror having a hole at its central part being provided for reflecting the illuminating light L from an illuminating system which is provided at a side of the same and leading said beam onto an optical axis on the object lens 1 so that said light is incident into an eye E being examined through the object lens 1. 3 is a photographing lens. 4 is a film plane. 5 is a mirror for a finder which is obliquely provided at an optical path in freely swingable manner. 6 is a mirror for turning the optical path. 7 is an ocuiar lens for a finder. 8 is an auxiliary lens of the present invention provided at an optical path in a freely inserted and pulled out manner.

Now explanations will be made in FIG. 1 on the relationship among the eye fundus and the pupil and imaging thereof in the above mentioned optical system. The illuminating light L from the illuminating system at a side forms an image of a light source at a central part $P_o$ of the holed mirror 2 then images at an eye pupil plane $E_p$ of an eye E being examined through the object lens 1 for illuminating an eye fundus $E_F$. When the focus of the object lens is on the eye fundus $E_F$, the pupil $E_p$ is imaged at the central part $P_o$ of the holed mirror 2 by the object lens 1 as shown by luminous flux 9 shown in the drawing. On the other hand the luminous flux 10 reflected from the eye fundus $E_F$ is imaged at the film plane 4 by the photographing lens 3 after being imaged near a rear focal plane $P_1$ behind the object lens 1. At that time if the mirror 5 is inserted in an optical path the light beam to be incident into the film plane 4 is reflected at the mirror 5 and after being further reflected at the optical path turning mirror 6 forms an image of the eye fundus $E_F$ at a point $P_2$ which has an optical path length of same distance as the optical path length from the mirror 5 to the film plane 4, so that the eye fundus $E_F$ can be observed through the ocular lens 7. What has been mentioned above is such photographing and observation of an eye fundus as being common to an eye-fundus camera of the present invention and to an eye-fundus camera of conventional type.

Figure 2:
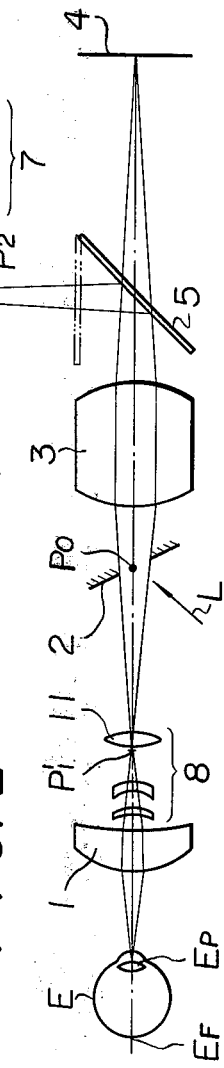
FIG. 2 is a drawing to explain a state wherein an auxiliary lens is inserted and an imaging relationship of the pupil image at said state.

In the present invention, as shown in FIG. 2 when the auxiliary lens 8 is inserted behind the object lens 1 so that the image of the pupil $E_p$ is formed at the same position $P'_1$ as the position $P_1$ where the image of the eye fundus $E_F$ is formed by the object lens 1 when the auxiliary lens (8) is not inserted as in FIG. 1, and the image of pupil formed at the position $P'_1$ is reimaged at same position $P'_2$ as the position $P_2$ in FIG. 1 through the photographing lens 3, the oblique mirror 5, etc., thus pupil alignment can be done while observing the pupil image through the ocular lens 7 of the finder system.

And in the operation of an alignment for the pupil instead of the illuminating light L from a side, ordinary external light is used. That is because when the auxiliary lens 8 is inserted and if the illuminating light L is used, the reflection of the illuminating light L by the auxiliary lens increases while the amount of light reflected at the pupil decreases, thus the pupil image becomes difficult to be observed. The illuminating light may be introduced into the optical system at a side of the object lens 1 from the auxiliary lens.

Therefore, in this eye-fundus camera, the auxiliary lens 8 is first inserted in an optical path to perform pupil alignment by a finder, then the auxiliary lens 8 is removed from the optical path to observe the eye fundus using the illuminating light L, further the oblique mirror 5 is removed from the optical path for proceeding to photographing onto the film plane 4 using stroboscopic light. A final lens 11 in the auxiliary lens 8 performs the function of a field lens and its position may be either in front or in rear of the position $P'_1$ as long as it is near the same. Also the mirror 2 for taking in the illuminating light does not have to be at the position of $P_o$, instead a diaphragm to reflect the illuminating light in a ring shape may be provided at the position of $P_o$, so that the light is concentrated thereinto as described, for example in U.S. Pat. No. 3,217,622.

Also when a scale is provided at the position of $P'_2$ in a finder system, it may be used as a pupil hole meter.

In the eye-fundus camera of the present invention mentioned above, an auxiliary lens is inserted in the optical path of a photographing optical system for directly observing the pupil of an eye to be examined with a finder of a camera. Therefore while pupil alignment becomes easy, exact position confirmation can be done by observing the pupil on the photographing optical path, thus the use of an eye-fundus camera becomes convenient.

What is claimed is:

1. An optical system for observation and photography of the eye-fundus in an eye-fundus camera, said system providing simplified pupil alignment, comprising:

an eye station for establishing the position of the eye;

an objective lens facing the eye-to-be-examined for forming an eye-fundus image at a point, $P_1$, along the optical axis of the optical system;

a photographic lens system disposed along the system optical axis on the side of the objective lens away from the eye beyond said eye-fundus image forming point, said photographic lens system for re-forming the eye-fundus image formed by the objective lens;

an eye-fundus-observing optical system, receptive to light passed by said photographic lens, for providing a focussed eye-fundus image for observation;

means for providing said reformed image of said eye-fundus to said observing optical system during observation and for providing said reformed image to an image plane during photography; and and optical alignment means for removable insertion into the optical system only during alignment, for providing the pupil image of the eye-to-be-examined at said point, $P_1$, along the system optical axis, said optical alignment means being disposed along the system optical axis between said objective lens and said observing optical system, said optical alignment means being removable from a position in the system optical axis to a position outside of the optical axis during observation and photography.

2. The optical system of claim 1 wherein said optical means is an auxiliary lens group.

3. The optical system of claim 2 wherein a reflecting mirror having a penetrating hole at its central part is arranged in the position where the pupil image of the eye-to-be-examined is formed by said object lens, an illuminating light beam being provided from the side of the optical axis of said optical system, said reflecting mirror including means for making said illuminating light beam reflect in a ring-band shape along the optical axis in the direction of said object lens, said ring-band shaped reflecting light beam passing through the objective lens and being incident on the eye-to-be-examined.

4. The optical system of claim 2 wherein a scale is provided as a pupil meter, said scale being provided, when the auxiliary lens is inserted, at the position of the pupil image of the eye-to-be-examined which is formed by the object lens and auxiliary lens.

5. The optical system of claim 2 wherein a scale is provided as a pupil meter, said scale being provided, when the auxiliary lens is inserted, at the position where the pupil image is reformed by the photographing lens.

6. The optical system of claim 2 wherein at least one of the lens systems constituting said auxiliary lens operates as a field lens, said field lens being arranged in the vicinity of the position where the pupil image of the eye to be examined is formed by the object lens and the auxiliary lens.

7. The optical system of claim 1 wherein a diaphragm is provided at the position where the pupil image of the eye-to-be-examined is formed by said object lens, an illuminating light beam being provided from the side of said optical system, the diaphragm including means for making the illuminating light beam incident from the side with regard to the optical axis of the eye-fundus camera to reflect in a ring-band shape in the direction of the object lens along the optical axis, said ring-band shaped, reflected light beam passing through the object lens and being incident on the eye-to-be-examined.

* * * * *